(12) United States Patent
Michihata et al.

(10) Patent No.: US 11,510,549 B2
(45) Date of Patent: Nov. 29, 2022

(54) MEDICAL IMAGE PROCESSING APPARATUS AND MEDICAL OBSERVATION SYSTEM

(71) Applicants: Sony Olympus Medical Solutions Inc., Tokyo (JP); Sony Corporation, Tokyo (JP)

(72) Inventors: Taihei Michihata, Kanagawa (JP); Satoshi Mitsui, Aichi (JP)

(73) Assignees: SONY OLYMPUS MEDICAL SOLUTIONS INC., Tokyo (JP); SONY CORPORATION, Tokyo (JP)

( * ) Notice: Subject to any disclaimer, the term of this patent is extended or adjusted under 35 U.S.C. 154(b) by 191 days.

(21) Appl. No.: 16/790,752

(22) Filed: Feb. 14, 2020

(65) Prior Publication Data
US 2020/0297185 A1   Sep. 24, 2020

(30) Foreign Application Priority Data

Mar. 22, 2019 (JP) .............................. JP2019-055707

(51) Int. Cl.
| | | |
|---|---|---|
| *A61B 1/00* | (2006.01) | |
| *A61B 1/05* | (2006.01) | |
| *A61B 1/06* | (2006.01) | |
| *G06T 3/40* | (2006.01) | |

(52) U.S. Cl.
CPC ...... *A61B 1/00009* (2013.01); *A61B 1/00186* (2013.01); *A61B 1/05* (2013.01); *A61B 1/0638* (2013.01); *G06T 3/4015* (2013.01)

(58) Field of Classification Search
CPC .............. A61B 1/00009; A61B 1/0005; A61B 1/00186; A61B 1/043; A61B 1/045; A61B 1/05; A61B 1/0638; G06T 3/4015
See application file for complete search history.

(56) References Cited

U.S. PATENT DOCUMENTS

| | | | |
|---|---|---|---|
| 10,335,014 B2 * | 7/2019 | Aoyama | ............ H04N 9/04559 |
| 2001/0007920 A1 * | 7/2001 | Hayashi | ............... A61B 1/0005 600/476 |
| 2001/0007921 A1 * | 7/2001 | Hayashi | ............. A61B 1/00186 600/478 |

(Continued)

FOREIGN PATENT DOCUMENTS

JP     2013-102899 A     5/2013

*Primary Examiner* — Peter D Le
(74) *Attorney, Agent, or Firm* — Xsensus LLP

(57) ABSTRACT

A medical image processing apparatus includes: image signal acquiring circuitry configured to acquire: a first image signal generated by capturing light of a first wavelength band with an image sensor; and a second image signal generated by capturing light of a second wavelength band different from the first wavelength band with the image sensor, the first image signal and the second image signal being not subjected to the demosaic processing, and the image sensor including a color filter in which filter groups having spectroscopic properties different from each other are arranged in a specific form; a first signal path including a demosaic processor configured to execute the demosaic processing to the first image signal; and a second signal path diverged from the first signal path on a path former part from the demosaic processor, in which the demosaic processing is not executed to the second image signal.

18 Claims, 10 Drawing Sheets

(56) References Cited

U.S. PATENT DOCUMENTS

| | | | |
|---|---|---|---|
| 2001/0009269 A1* | 7/2001 | Hayashi | A61B 1/00186 |
| | | | 250/458.1 |
| 2001/0049473 A1* | 12/2001 | Hayashi | A61B 5/0084 |
| | | | 600/317 |
| 2009/0160992 A1* | 6/2009 | Inaba | H04N 9/04557 |
| | | | 348/308 |
| 2013/0041221 A1* | 2/2013 | McDowall | H04N 13/243 |
| | | | 348/E9.037 |
| 2014/0062882 A1* | 3/2014 | Ozawa | G06F 3/038 |
| | | | 345/158 |
| 2015/0201871 A1* | 7/2015 | Shiraishi | A61B 5/1459 |
| | | | 600/339 |
| 2015/0272422 A1* | 10/2015 | Aoyama | H04N 9/04559 |
| | | | 348/68 |
| 2015/0366444 A1* | 12/2015 | Morimoto | A61B 1/0638 |
| | | | 600/339 |
| 2016/0065926 A1* | 3/2016 | Nonaka | H04N 5/2351 |
| | | | 348/164 |
| 2016/0287061 A1* | 10/2016 | Shigeta | A61B 1/0638 |
| 2018/0041714 A1* | 2/2018 | Hayashi | H04N 5/332 |
| 2018/0228347 A1* | 8/2018 | Yamamoto | A61B 1/000094 |
| 2019/0098188 A1* | 3/2019 | Zhu | H04N 5/23245 |
| 2020/0221028 A1* | 7/2020 | Kobayashi | H04N 5/2353 |

* cited by examiner

MEDICAL IMAGE PROCESSING APPARATUS AND MEDICAL OBSERVATION SYSTEM

This application claims priority from Japanese Application No. 2019-055707, filed on Mar. 22, 2019, the contents of which are incorporated by reference herein in its entirety.

BACKGROUND

The present disclosure relates to a medical image processing apparatus and a medical observation system.

In the related art, in a medical observation system in which the inside of the biological body (an observation target) that is an object is captured (observed), a system is known in which each light ray of a first wavelength band and a second wavelength band described below is captured by an image sensor (for example, refer to JP 2013-102899 A).

The light of the first wavelength band is white light. That is, in the image sensor, the observation target is irradiated with the white light, and the white light reflected on the observation target is captured, and thus, a first RAW image signal is output.

The light of the second wavelength band is fluorescence that is emitted from the observation target when the observation target is irradiated with excitation light that excites a fluorescent substance such as indocyanine green. Then, in the image sensor, the fluorescence is captured, and thus, a second RAW image signal is output.

Note that, a color filter in which filter groups of red (R), green (G), and blue (B) having spectroscopic properties different from each other are arranged in a specific form is provided on a light receiving surface of the image sensor. That is, the first RAW image signal and the second RAW image signal include component information (pixel data) of any of R, G, and B corresponding to each of the filter groups of R, G, and B for each pixel.

Hereinafter, the component information of R will be referred to as an r value, the component information of G will be referred to as a g value, and the component information of B will be referred to as a b value.

SUMMARY

In the medical observation system described in JP 2013-102899 A, image processing is executed with respect to each of the first RAW image signal and the second RAW image signal.

Here, it is considered that the first RAW image signal is subjected to demosaic processing in which all of the r value, the g value, and the b value are provided for each pixel by interpolation, and YC processing in which a luminance color difference signal is generated by using an image signal after the demosaic processing. On the other hand, as with the first RAW image signal, it is also considered that the second RAW image signal is subjected to the demosaic processing and the YC processing. However, in a case where the demosaic processing is executed with respect to the second RAW image signal, pixel data generated by the interpolation (in practice, pixel data other than the r value, the g value, and the b value detected by the image sensor) is used at the time of generating the luminance color difference signal, and thus, the sharpness of a fluorescent image that is an image based on the second RAW image signal and is used in the observation decreases. Therefore, there is a need for a technique in which an image suitable for observation may be generated.

There is a need for a medical image processing apparatus and a medical observation system in which an image suitable for observation may be generated.

According to one aspect of the present disclosure, there is provided a medical image processing apparatus including: image signal acquiring circuitry configured to acquire: a first image signal generated by capturing light of a first wavelength band with an image sensor; and a second image signal generated by capturing light of a second wavelength band different from the first wavelength band with the image sensor, the first image signal and the second image signal being not subjected to the demosaic processing, and the image sensor including a color filter in which a plurality of filter groups having spectroscopic properties different from each other are arranged in a specific form on a light receiving surface of the image sensor; a first signal path including a demosaic processor configured to execute the demosaic processing to the first image signal acquired by the image signal acquiring circuitry and input into the first signal path; and a second signal path diverged from the first signal path on a path former part from the demosaic processor, in which the demosaic processing is not executed to the second image signal acquired by the image signal acquiring circuitry and input into the second signal path.

DETAILED DESCRIPTION

Figure 1:
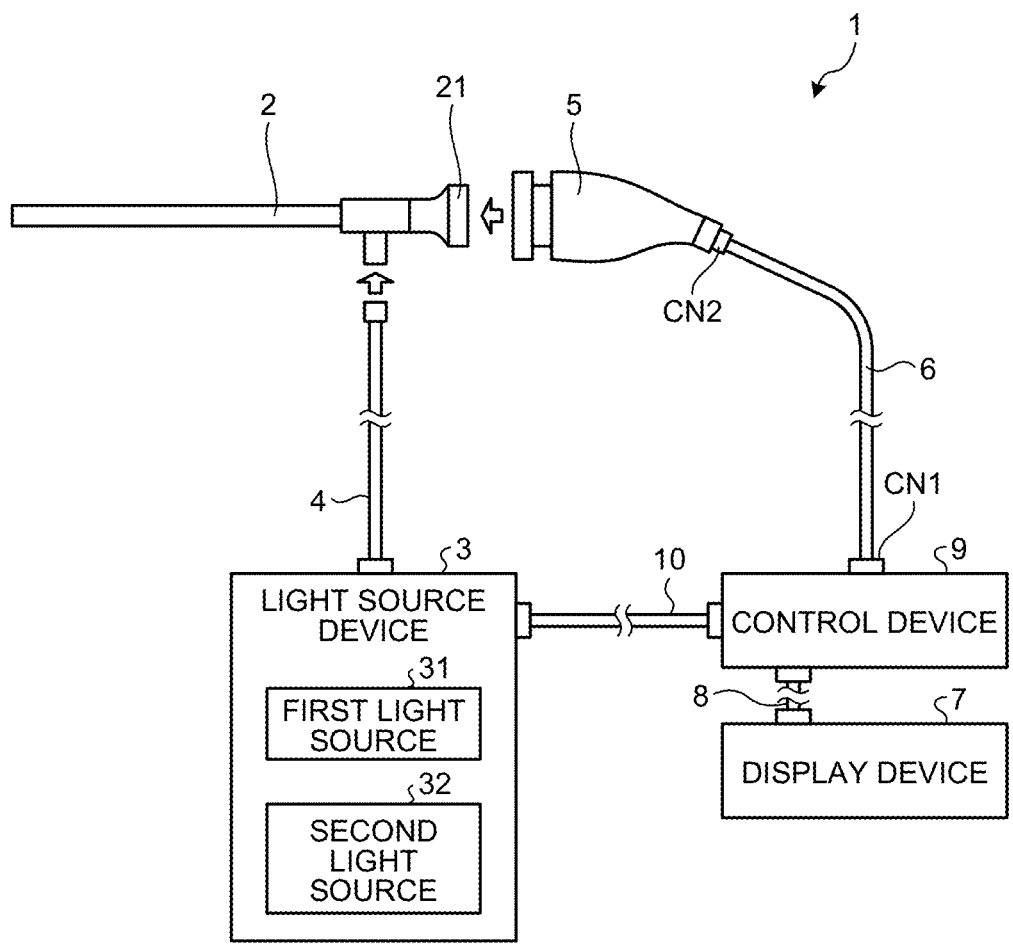
FIG. 1 is a diagram illustrating a configuration of a medical observation system according to an embodiment.

Hereinafter, a mode for carrying out the present disclosure (hereinafter, an embodiment) will be described with reference to the drawings. Note that, the present disclosure is not limited to the embodiment described below. Further, in the description of the drawings, the same reference numerals will be applied to the same parts.

Schematic Configuration of Medical Observation System

FIG. 1 is a diagram illustrating the configuration of a medical observation system 1 according to this embodiment.

The medical observation system 1 is a system used in a medical field, in which the inside of the biological body (an observation target) that is an object is captured (observed). As illustrated in FIG. 1, the medical observation system 1 includes an insertion portion 2, a light source device 3, a light guide 4, a camera head 5, a first transmission cable 6, a display device 7, a second transmission cable 8, a control device 9, and a third transmission cable 10.

In this embodiment, the insertion portion 2 includes a rigid endoscope. That is, the insertion portion 2 has an elongated shape in which the entire part is rigid, or a part is flexible and the other part is rigid, and is inserted into the biological body. In the insertion portion 2, an optical system that is configured by using one or a plurality of lenses and condenses light from the object is provided.

One end of the light guide 4 is connected to the light source device 3, and light to be emitted into the biological body is supplied to one end of the light guide 4, under the control of the control device 9. As illustrated in FIG. 1, the light source device 3 includes a first light source 31 and a second light source 32.

The first light source 31 allows normal light of a first wavelength band that is a visible wavelength band to exit (to be emitted). In this embodiment, the first light source 31 includes a light emitting diode (LED) that emits white light.

The second light source 32 allows excitation light of a third wavelength band that is different from the first wavelength band to exit (to be emitted). In this embodiment, the second light source 32 includes a semiconductor laser that emits near-infrared excitation light of a near-infrared wavelength band. The near-infrared excitation light is excitation light that excites a fluorescent substance such as indocyanine green. In addition, in a case where the fluorescent substance such as indocyanine green is excited by the near-infrared excitation light, fluorescence of a second wavelength band that is a wavelength band other than a visible range, having a central wavelength on a long wavelength side from the central wavelength of the wavelength band of the near-infrared excitation light, is emitted. Note that, the wavelength band of the near-infrared excitation light and the wavelength band of the fluorescence may be set such that the wavelength bands overlap each other in a part, or may be set such that the wavelength bands do not overlap each other.

Then, in the light source device 3 according to this embodiment, in a first period and second period that are alternately repeated, the first light source 31 is driven in the first period, under the control of the control device 9. That is, in the first period, the light source device 3 emits the normal light (the white light). In addition, in the light source device 3, in the second period, the second light source 32 is driven, under the control of the control device 9. That is, in the second period, the light source device 3 emits the near-infrared excitation light.

Note that, in this embodiment, the light source device 3 is configured separately from the control device 9, but the present disclosure is not limited thereto, and a configuration in which the control device 9 is provided inside may be adopted.

One end of the light guide 4 is detachably connected to the light source device 3, and the other end is detachably connected to the insertion portion 2. Then, the light guide 4 transmits light that is supplied from the light source device 3 (the normal light or the near-infrared excitation light) to the other end from one end, and supplies the light to the insertion portion 2. In a case where the inside of the biological body is irradiated with the normal light (the white light), the normal light through the inside of the biological body (the normal light reflected on the inside of the biological body) is condensed by the optical system in the insertion portion 2. In addition, in a case where the inside of the biological body is irradiated with the near-infrared excitation light, the near-infrared excitation light through the inside of the biological body (the near-infrared excitation light reflected on the inside of the biological body), and the fluorescence emitted from the fluorescent substance by exciting the fluorescent substance such as indocyanine green that is integrated in an affected area in the biological body, with the near-infrared excitation light, are condensed by the optical system in the insertion portion 2.

The camera head 5 corresponds to an imaging device according to the present disclosure. The camera head 5 is detachably connected to a proximal end of the insertion portion 2 (an eye piece 21 (FIG. 1)). Then, the camera head 5 captures the light that is condensed by the insertion portion 2, and outputs an image signal (a RAW signal) according to the imaging, under the control of the control device 9. The image signal, for example, is an image signal of 4 K or higher.

Note that, the detailed configuration of the camera head 5 will be described below.

One end of the first transmission cable 6 is detachably connected to the control device 9 through a connector CN1 (FIG. 1), and the other end is detachably connected to the camera head 5 through a connector CN2 (FIG. 1). Then, the first transmission cable 6 transmits the image signal or the like that is output from the camera head 5 to the control device 9, and transmits each of a control signal, a synchronization signal, a clock, power, and the like that are output from the control device 9 to the camera head 5.

Note that, in a case where the image signal or the like is transmitted to the control device 9 from the camera head 5 through the first transmission cable 6, the image signal or the like may be transmitted as an optical signal, or may be transmitted as an electric signal. The same applies to a case where the control signal, the synchronization signal, and the clock are transmitted to the camera head 5 from the control device 9 through the first transmission cable 6.

The display device 7 includes a display using a liquid crystal or organic electro luminescence (EL), and the like, and displays an image based on a video signal from the control device 9, under the control of the control device 9.

One end of the second transmission cable 8 is detachably connected to the display device 7, and the other end is detachably connected to the control device 9. Then, the second transmission cable 8 transmits the video signal that is processed by the control device 9 to the display device 7.

The control device 9 corresponds to a medical image processing apparatus according to the present disclosure. The control device 9 includes a central processing unit (CPU), a field-programmable gate array (FPGA), or the like, and comprehensively controls the operation of the light source device 3, the camera head 5, and the display device 7.

Note that, the detailed configuration of the control device 9 will be described below.

One end of the third transmission cable 10 is detachably connected to the light source device 3, and the other end is detachably connected to the control device 9. Then, the third transmission cable 10 transmits the control signal from the control device 9 to the light source device 3.

Configuration of Camera Head Next, the configuration of the camera head 5 will be described.

Figure 2:
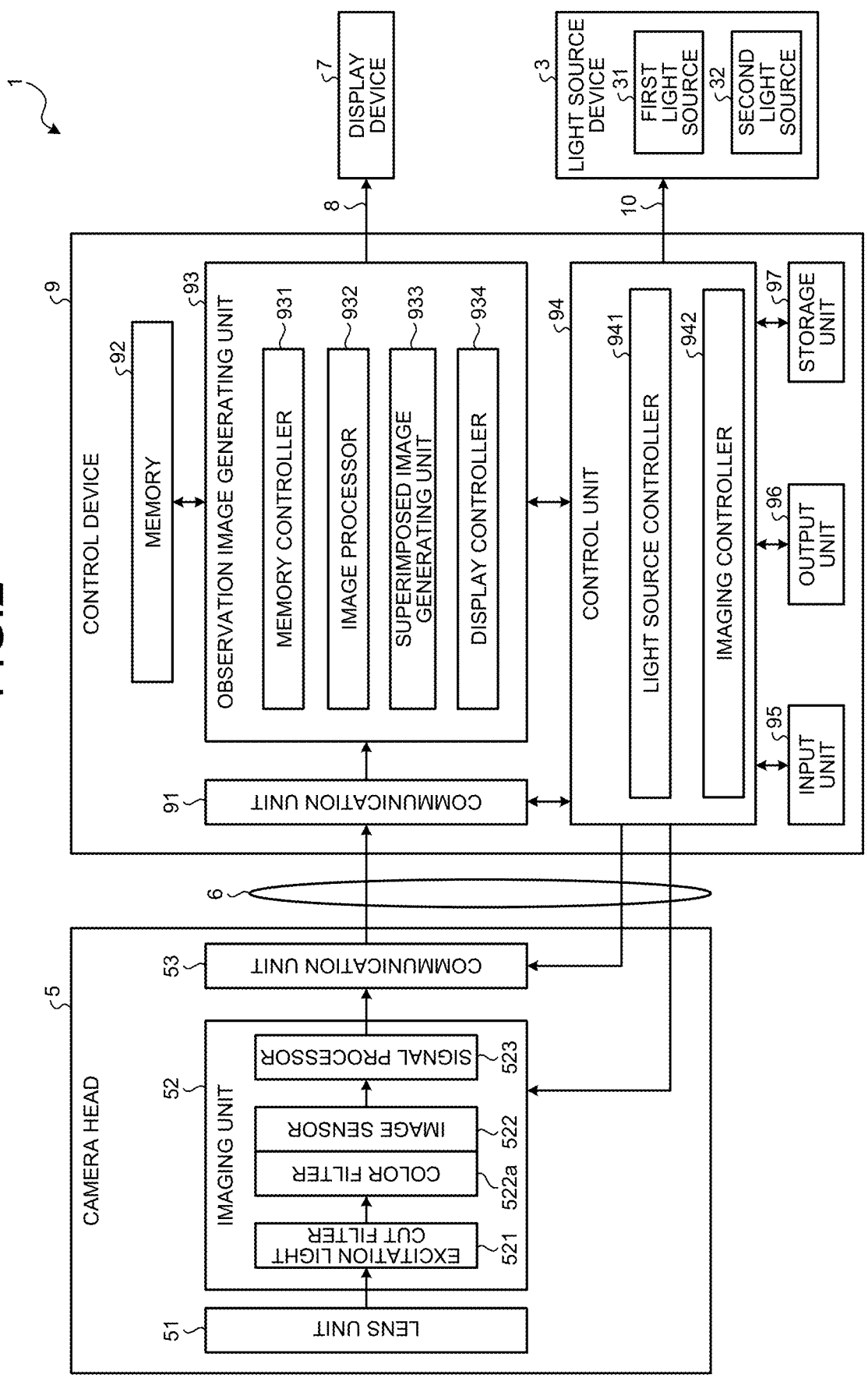
FIG. 2 is a block diagram illustrating a configuration of a camera head and a control device.

FIG. 2 is a block diagram illustrating the configuration of the camera head 5 and the control device 9.

Note that, in FIG. 2, for the convenience of the description, the connectors CN1 and CN2 between the control device 9 and the camera head 5, and the first transmission cable 6, a connector between the control device 9 and the display device 7, and the second transmission cable 8, and a connector between the control device 9 and the light source device 3, and the third transmission cable 10 are not illustrated.

As illustrated in FIG. 2, the camera head 5 includes a lens unit 51, an imaging unit 52, and a communication unit 53.

The lens unit 51 is configured by using one or a plurality of lenses, and forms an image with the light that is condensed by the insertion portion 2 (the normal light or the near-infrared excitation light, and the fluorescence) on an imaging surface of the imaging unit 52 (an image sensor 522).

The imaging unit 52 captures the inside of the biological body, under the control of the control device 9. As illustrated in FIG. 2, the imaging unit 52 includes an excitation light cut filter 521, an image sensor 522, and a signal processor 523.

The excitation light cut filter 521 is provided between the lens unit 51 and the image sensor 522, and includes a band stop filter that removes a specific wavelength band. Note that, hereinafter, for the convenience of the description, a wavelength band that is cut (removed) by the excitation light cut filter 521 will be referred to as a cut band, a wavelength band that is on a short wavelength side from the cut band and is transmitted through the excitation light cut filter 521 will be referred to as a short wavelength side transmission region, and a wavelength band that is on a long wavelength side from the cut band and is transmitted through the excitation light cut filter 521 will be referred to as a long wavelength side transmission region.

Here, the cut band includes at least a part of the wavelength band of the near-infrared excitation light. In this embodiment, the cut band includes the entire wavelength band of the near-infrared excitation light. In addition, the long wavelength side transmit band includes the wavelength band of the fluorescence. Further, the short wavelength side transmission region includes the wavelength band of the normal light (the white light).

That is, the excitation light cut filter 521 transmits the normal light (the white light) that is directed towards the image sensor 522 from the lens unit 51. Note that, hereinafter, for the convenience of the description, the normal light (the white light) that is transmitted through the excitation light cut filter 521 and is directed towards the image sensor 522 will be referred to as an object picture. On the other hand, in the near-infrared excitation light and the fluorescence that is directed towards the image sensor 522 from the lens unit 51, the excitation light cut filter 521 removes the near-infrared excitation light, and transmits the fluorescence. Note that, hereinafter, for the convenience of the description, the fluorescence that is transmitted through the excitation light cut filter 521 and is directed towards the image sensor 522 will be referred to as a fluorescent picture.

The image sensor 522 includes a charge coupled device (CCD), a complementary metal oxide semiconductor (CMOS), or the like that receives the object picture or the fluorescent picture transmitted through the excitation light cut filter 521, and converts the image into an electric signal (an analog signal). A color filter 522a (FIG. 2) is provided on the imaging surface (the light receiving surface) of the image sensor 522.

Figure 3:
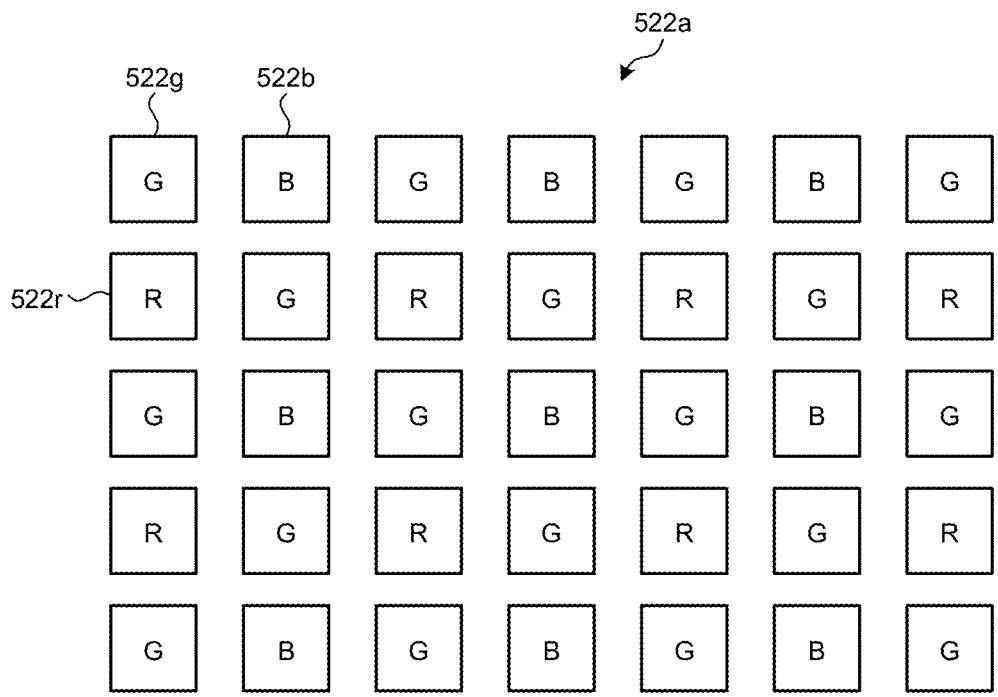
FIG. 3 is a diagram illustrating a color filter.
Figure 4:
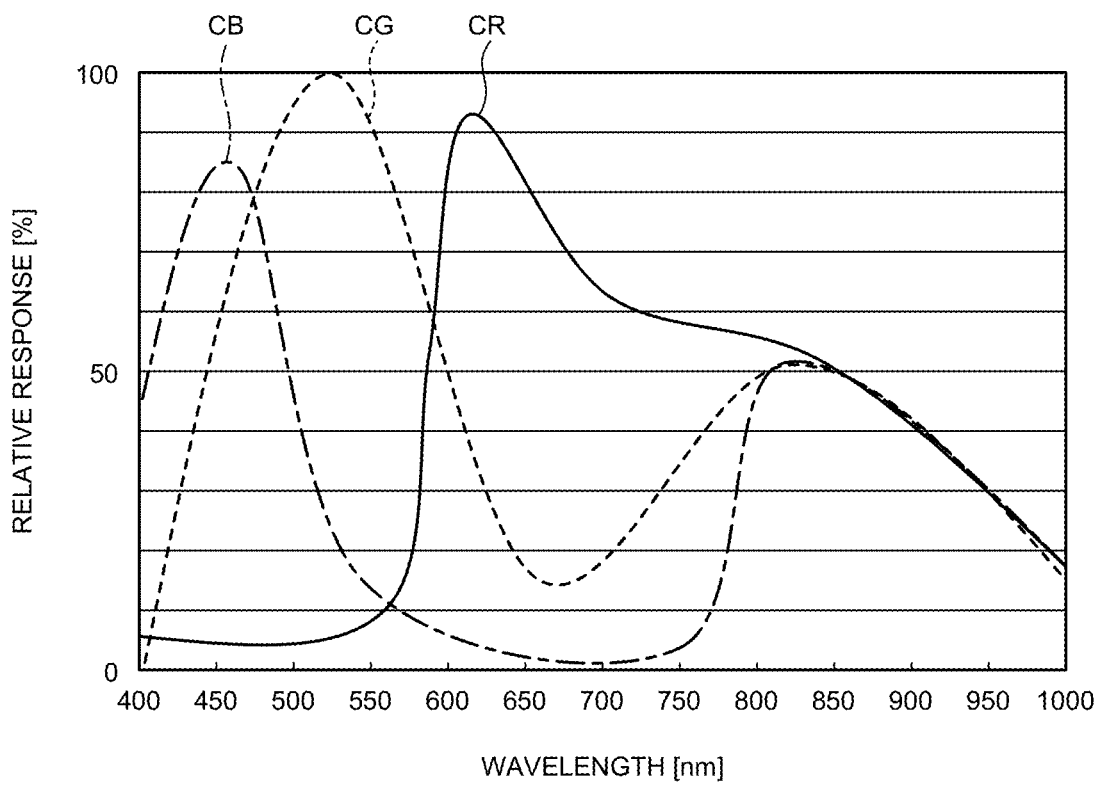
FIG. 4 is a diagram illustrating spectroscopic properties of the color filter.

FIG. 3 is a diagram illustrating the color filter 522a. FIG. 4 is a diagram illustrating spectroscopic properties of the color filter 522a. Specifically, in FIG. 4, spectroscopic properties of an R filter group 522r are illustrated by a curve CR, spectroscopic properties of the G filter group 522g are illustrated by a curve CG, and spectroscopic properties of the B filter group 522b are illustrated by a curve CB.

The color filter 522a is a color filter in which three filter groups that are grouped in accordance with the wavelength band of the transmitted light (red (R), green (G), and blue (B)) are arranged in a specific form (for example, a Bayer array).

Specifically, as illustrated in FIG. 3 and FIG. 4, the color filter 522a includes the R filter group 522r (FIG. 3) that mainly transmits light of an R wavelength band (corresponding to a first visible wavelength band and a second visible wavelength band according to the present disclosure), the B filter group 522b (FIG. 3) that mainly transmits light of a B wavelength band (corresponding to the first visible wavelength band and the second visible wavelength band according to the present disclosure), a first G filter group (arranged in the same column as that of the R filter group 522r) that mainly transmits light of a G wavelength band (corresponding to the first visible wavelength band and the second visible wavelength band according to the present disclosure), and a second G filter group (arranged in the same column as that of the B filter group 522b) that mainly transmits the light of the G wavelength band (corresponding to the first visible wavelength band and the second visible wavelength band according to the present disclosure). Note that, in FIG. 3, the first G filter group and the second G filter group are collectively illustrated as the G filter group 522g. In addition, in FIG. 3, a letter "R" is applied to the R filter group 522r, a letter "G" is applied to the G filter group 522g, and a letter "B" is applied to the B filter group 522b.

Note that, as illustrated in FIG. 4, each of the filter groups 522r, 522g, and 522b of R, G, and B has approximately the same spectroscopic properties in the wavelength band of the fluorescence (the second wavelength band, for example, a wavelength band of approximately 850 nm to 900 nm). Then, the image sensor 522 has a sensitivity with respect not only the light of the R, G, and B wavelength bands, but also the wavelength band of the fluorescence (the second wavelength band).

Note that, each of the filter groups 522r, 522g, and 522b of R, G, and B corresponds to a first filter group and a second filter group according to the present disclosure.

Then, the image sensor 522 performs imaging in synchronization with a light emitting timing of the light source device 3, in each of a first period and a second period that are alternately repeated, under the control of the control device 9. Hereinafter, for the convenience of the description, an image that is generated by capturing the object picture (the normal light) with the image sensor 522 in the first period will be referred to as an object image (corresponding to a first image signal according to the present disclosure), and an image that is generated by capturing the fluorescent picture (the fluorescence) with the image sensor 522 in the second period will be referred to as a fluorescent image (corresponding to a second image signal according to the present disclosure). In addition, the object image and the fluorescent image will be collectively referred to as a RAW captured image.

The signal processor 523 performs signal processing with respect to the RAW captured image (an analog signal) that is generated by the image sensor 522, and outputs the RAW captured image (a digital signal).

The communication unit 53 functions as a transmitter that transmits the RAW captured image output from the imaging unit 52 to the control device 9 through the first transmission cable 6. The communication unit 53, for example, includes a high-speed serial interface that performs communication of the RAW captured image with respect to the control device 9 through the first transmission cable 6, at a transmission rate of greater than or equal to 1 Gbps.

Configuration of Control Device

Next, the configuration of the control device 9 will be described with reference to FIG. 2.

As illustrated in FIG. 2, the control device 9 includes a communication unit 91, a memory 92, an observation image generating unit 93, a control unit 94, an input unit 95, an output unit 96, and a storage unit 97. The communication unit 91 functions as a receiver that receives the RAW captured image output from the camera head 5 (the communication unit 53) through the first transmission cable 6. The communication unit 91, for example, may include the high-speed serial interface that performs the communication of the RAW captured image with respect to the communication unit 53, at a transmission rate of greater than or equal to 1 Gbps. That is, the communication unit 91 corresponds to an image signal acquiring unit according to the present disclosure.

The memory 92, for example, includes a dynamic random access memory (DRAM), and the like. The memory 92 is capable of temporarily storing the RAW captured image that is sequentially output from the camera head 5 (the communication unit 53) for a plurality of frames.

The observation image generating unit 93 processes the RAW captured image that is sequentially output from the camera head 5 (the communication unit 53) and is received by the communication unit 91, under the control of the control unit 94. As illustrated in FIG. 2, the observation image generating unit 93 includes a memory controller 931, an image processor 932, a superimposed image generating unit 933, and a display controller 934.

The memory controller 931 controls the writing and the reading of the RAW captured image with respect to the memory 92. More specifically, the memory controller 931 sequentially writes the RAW captured image (the object image and the fluorescent image) that is sequentially output from the camera head 5 (the communication unit 53) and is received by the communication unit 91 in the memory 92. In addition, the memory controller 931 alternately reads out the object image and the fluorescent image from the memory 92 at a specific timing, and sequentially inputs the object image and the fluorescent image that are read out into the image processor 932.

Note that, in this embodiment, the RAW captured image that is generated by the imaging unit 52 is directly input into the image processor 932, but the image that is input into the image processor 932 is not limited to the RAW captured image, and may be other images insofar as the image is an image before demosaic processing.

Figure 5:
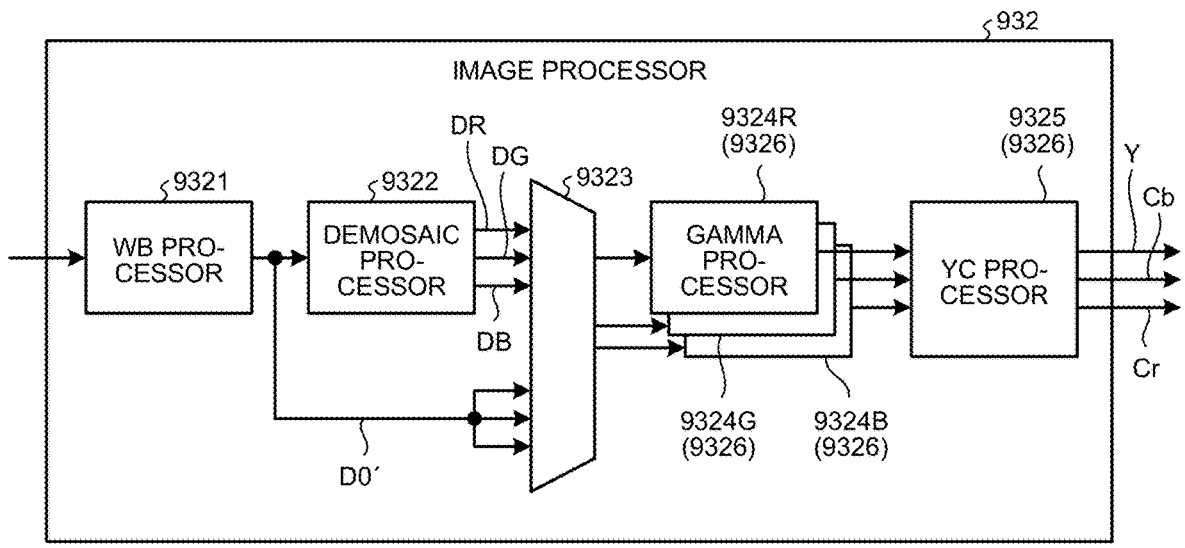
FIG. 5 is a block diagram illustrating a configuration of an image processor.
Figure 6:
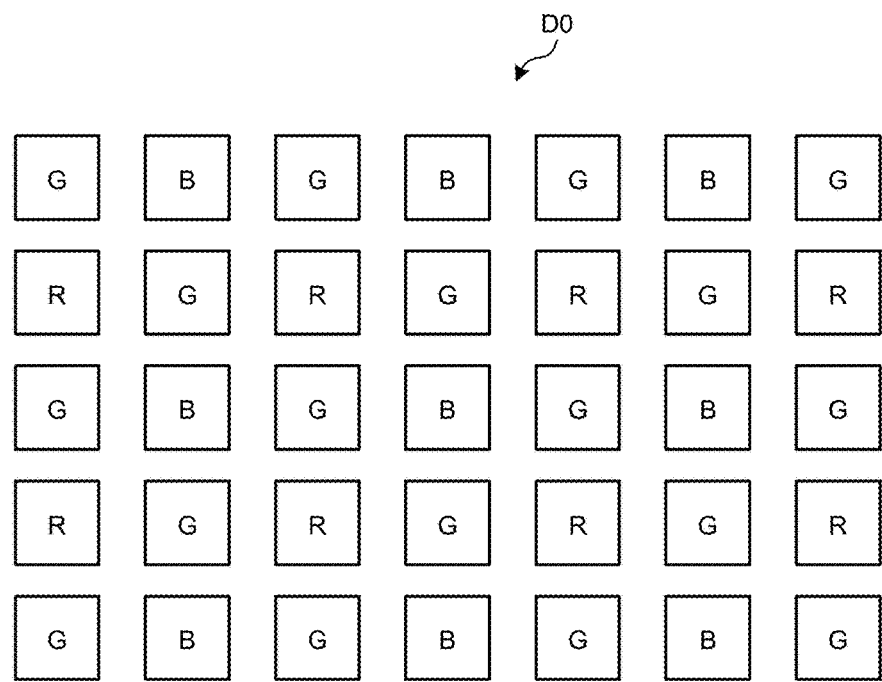
FIG. 6 is a diagram illustrating a RAW captured image.

FIG. 5 is a block diagram illustrating the configuration of the image processor 932. FIG. 6 is a diagram illustrating a RAW captured image D0.

The image processor 932 executes the image processing with respect to each of the input RAW captured images D0 (the object image and the fluorescent image). As illustrated in FIG. 5, the image processor 932 includes a WB processor 9321, a demosaic processor 9322, a selector 9323, three gamma processors 9324R, 9324G, and 9324B, and a YC processor 9325.

Here, as illustrated in FIG. 6, the RAW captured image D0 includes component information (pixel data) of any of R, G, and B respectively corresponding to the filter groups 522r, 522g, and 522b of R, G, and B for each pixel. Note that, in FIG. 6, a letter of "R" is applied to a pixel including component information of R (hereinafter, referred to as an r value), a letter "G" is applied to a pixel including component information of G (hereinafter, referred to as a g value), a letter "B" is applied to a pixel including component information of B (hereinafter, referred to as a b value).

The WB processor 9321 corresponds to a white balance adjustment processor and an output unit according to the present disclosure. The WB processor 9321 performs WB processing (white balance adjustment processing) of multiplying each of the r value, the g value, and the b value in the RAW captured image D0 (the object image and the fluorescent image) by a specific gain that is set by the control unit 94. Note that, three gains to be respectively multiplied by the r value, the g value, and the b value in the object image (hereinafter, referred to as a first gain) are different from three gains to be respectively multiplied by the r value, the g value, and the b value in the fluorescent image (hereinafter, referred to as a second gain). Specifically, three first gains are a gain for obtaining a white balance of the r value, the g value, and the b value in the wavelength band of the normal light (the white light) (the first wavelength band). On the other hand, three second gain are a gain for obtaining a white balance of the r value, the g value, and the b value in the wavelength band of the fluorescence (the second wavelength band).

Figure 7:
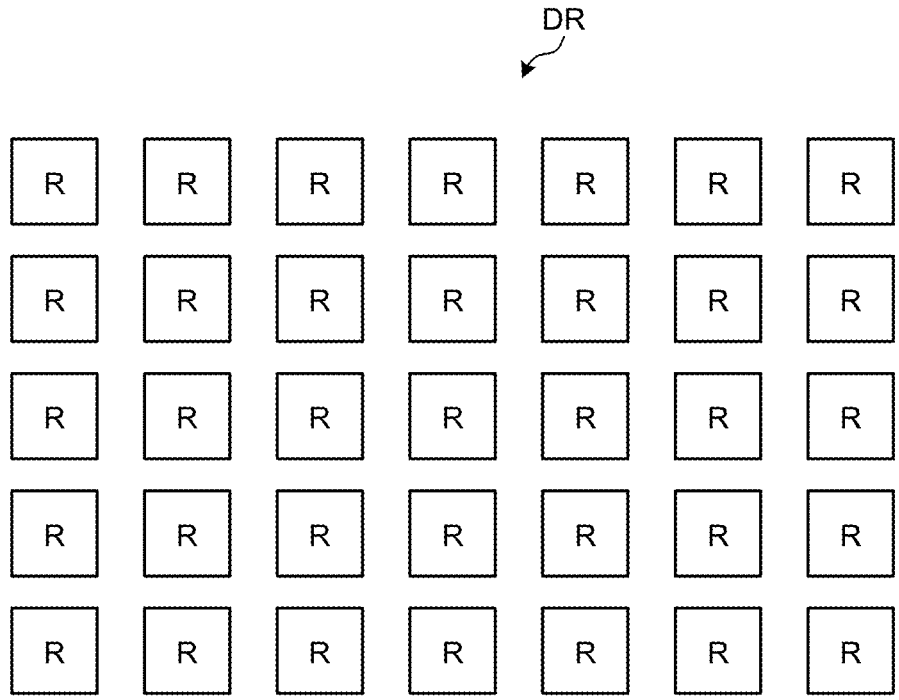
FIG. 7 is a diagram illustrating an R captured image that is generated by demosaic processing.
Figure 8:
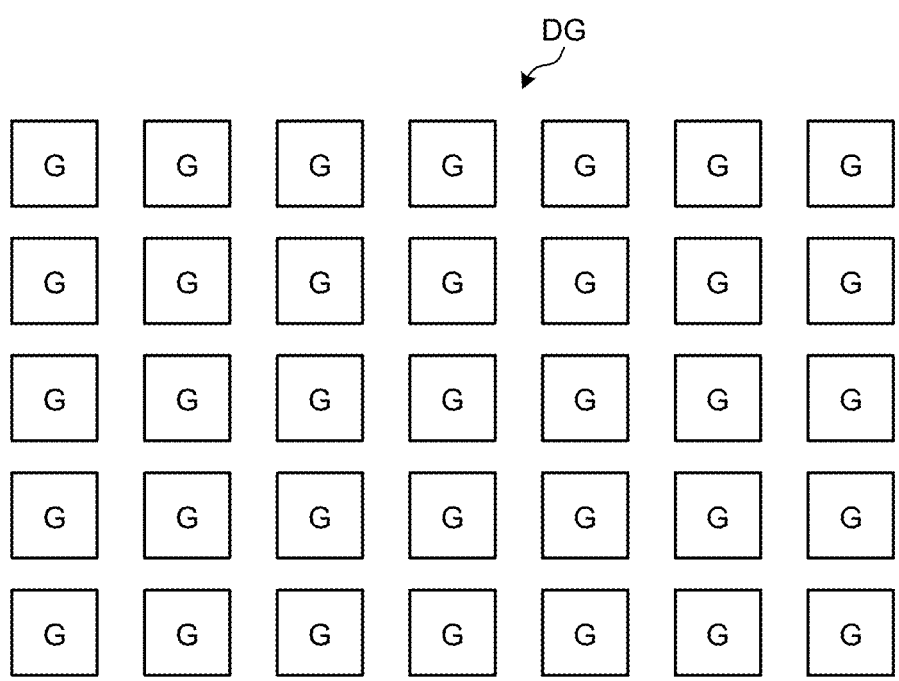
FIG. 8 is a diagram illustrating a G captured image that is generated by the demosaic processing.
Figure 9:
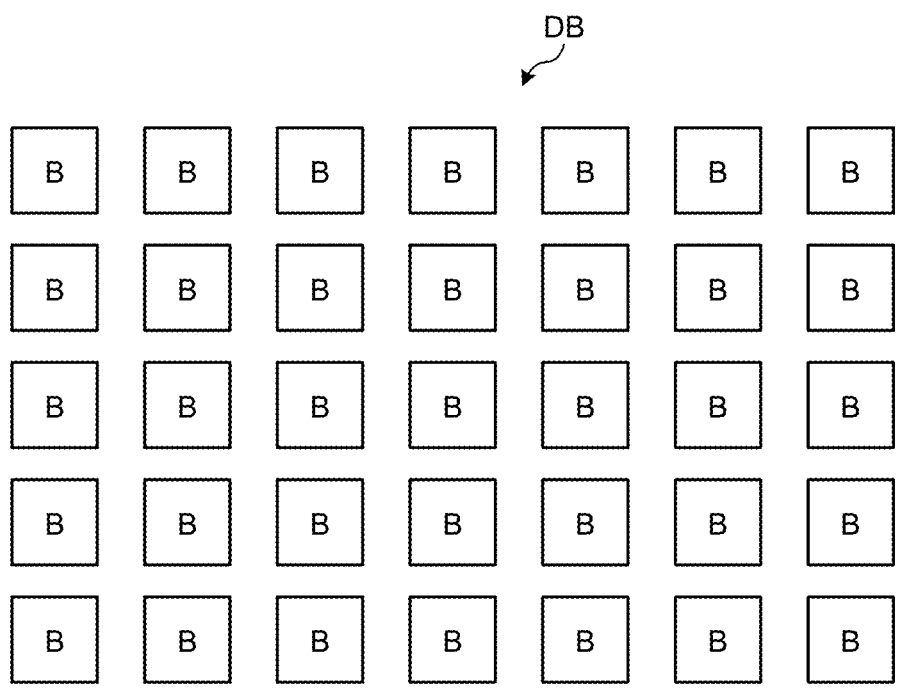
FIG. 9 is a diagram illustrating a B captured image that is generated by the demosaic processing.

FIG. 7 is a diagram illustrating an R captured image DR that is generated by the demosaic processing. FIG. 8 is a diagram illustrating a G captured image DG that is generated by the demosaic processing. FIG. 9 is a diagram illustrating a B captured image DB that is generated by the demosaic processing. Note that, in FIG. 7 to FIG. 9, as with FIG. 6, the letter "R" is applied to the pixel including the r value, the letter "G" is applied to the pixel including the g value, and the letter "B" is applied to the pixel including the b value.

The demosaic processor 9322 generates the R captured images DR (FIG. 7) respectively having the r value for all of the pixels by interpolation, the G captured images DG (FIG. 8) respectively having the g value for all of the pixels by interpolation, and the B captured images DB (FIG. 9) respectively having the b value for each of the pixels by interpolation, from the object image after the WB processing.

The R, G, and B captured images DR, DG, and DB described above correspond to a demosaic image signal according to the present disclosure.

The selector 9323 corresponds to a selector according to the present disclosure. The selector 9323 outputs three images of one set in a set of three R, G, and B captured images DR, DG, and DB that are input from the demosaic processor 9322 and a set of three fluorescent images D0' (FIG. 5) after the WB processing that are input from the WB processor 9321, under the control of the control unit 94.

Note that, three fluorescent images D0' after the WB processing are an image having only any one of the r value, the g value, and the b value in one pixel, without being subjected to the demosaic processing, and are identical to each other. In addition, three fluorescent images D0' after the WB processing correspond to a second image signal according to the present disclosure.

Three gamma processors 9324R, 9324G, and 9324B perform gamma processing (γ correction) with respect to each of three images (three R, G, and B captured images DR, DG, and DB or three fluorescent images D0') that are output from the selector 9323. In this embodiment, three gamma processors 9324R, 9324G, and 9324B execute the same gamma processing.

The YC processor 9325 performs calculation in a specific arithmetic expression by using three images (three R, G, and B captured images DR, DG, and DB or three fluorescent images D0') that are output from the selector 9323 and are subjected to the gamma processing, and thus, generates a luminance signal Y (FIG. 5) and color difference signals Cb and Cr (FIG. 5). More specifically, the YC processor 9325 performs calculation in the specific arithmetic expression by using three R, G, and B captured images DR, DG, and DB that are output from the selector 9323 and are subjected to the gamma processing, and thus, generate first luminance color difference signals Y, Cb, and Cr. On the other hand, the YC processor 9325 performs calculation in the specific arithmetic expression by using three fluorescent images D0' that are output from the selector 9323 and are subjected to the gamma processing, and thus, generates second luminance color difference signals Y, Cb, and Cr. Note that, in a case where calculation is performed in the specific arithmetic expression from three fluorescent images D0' that are output from the selector 9323 and are subjected to the gamma processing, each of the color difference signals Cb and Cr is a signal indicating approximately 0.

Three gamma processors 9324R, 9324G, and 9324B and the YC processor 9325 described above correspond to a signal generating unit 9326 (FIG. 5) according to the present disclosure. Then, the selector 9323 is provided between the demosaic processor 9322 and the signal generating unit 9326.

As described above, a first signal path for processing the input RAW captured image D0 (the object image) and a second signal path for processing the input RAW captured image D0 (the fluorescent image) are provided in the image processor 932. The first signal path is a path following the WB processor 9321 to the demosaic processor 9322 to the selector 9323 to three gamma processors 9324R, 9324G, and 9324B to the YC processor 9325. On the other hand, the second signal path is a path following the WB processor 9321 to the selector 9323 to three gamma processors 9324R, 9324G, and 9324B to the YC processor 9325. That is, the second signal path is a path that is diverged from the first signal path on a path former part from the demosaic processor 9322, is converged into the first signal path on a path latter part from the demosaic processor 9322, in which the demosaic processing is not executed. Then, a signal generating unit 9326 is provided in a path to which the first signal path and the second signal path are converged.

Hereinafter, for the convenience of the description, image processing following the first signal path described above will be referred to as first image processing, and image processing following the second signal path described above will be referred to as second image processing.

A superimposed image generating unit 933 generates a superimposed image by superimposing an object image after being subjected to the first image processing by the image processor 932, and a fluorescent image after being subjected to the second image processing by the image processor 932 in pixels corresponding to the entire region.

The display controller 934 generates a video signal for display, based on the superimposed image that is generated by the superimposed image generating unit 933. Then, the display controller 934 outputs the video signal to the display device 7 through the second transmission cable 8.

The control unit 94, for example, is configured by using a CPU, an FPGA, or the like, outputs the control signal through the first to third transmission cables 6, 8, and 10, and thus, controls the operation of the light source device 3, the camera head 5, and the display device 7, and controls the entire operation of the control device 9. As illustrated in FIG. 2, the control unit 94 includes a light source controller 941 and an imaging controller 942. Note that, the function of the light source controller 941 and the imaging controller 942 will be described in "Operation of Control Device" described below.

The input unit 95 is configured by using a manipulation device such as a mouse, a keyboard, and a touch panel, and receives a user manipulation of a user such as a medical doctor. Then, the input unit 95 outputs a manipulation signal corresponding to the user manipulation to the control unit 94.

The output unit 96 is configured by using a speaker, a printer, or the like, and outputs various information items.

The storage unit 97 stores a program that is executed by the control unit 94, information for the processing of the control unit 94, or the like.

Operation of Control Device

Next, the operation of the control device 9 described above will be described.

Figure 10:
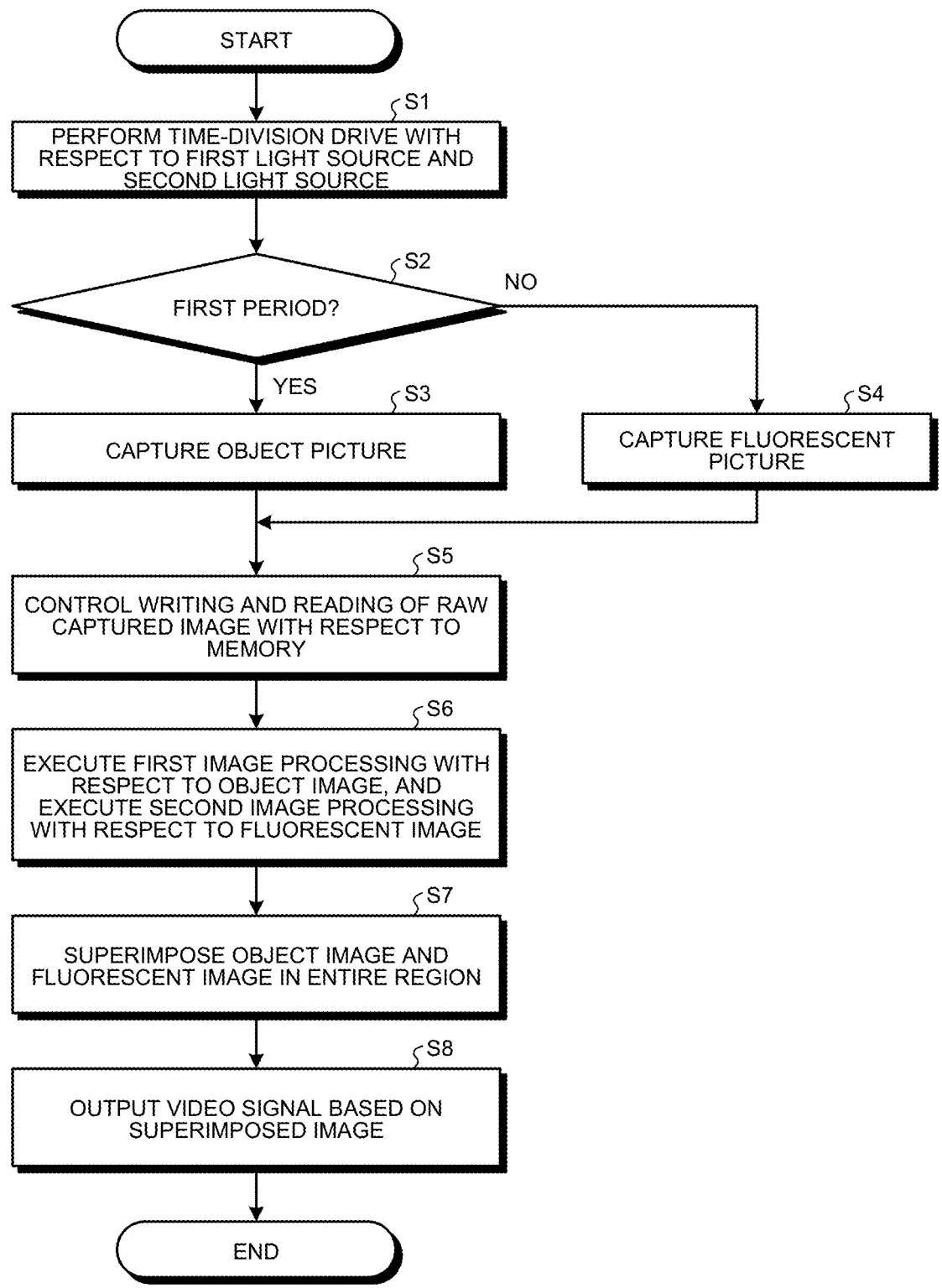
FIG. 10 is a flowchart illustrating an operation of the control device.
Figure 11:
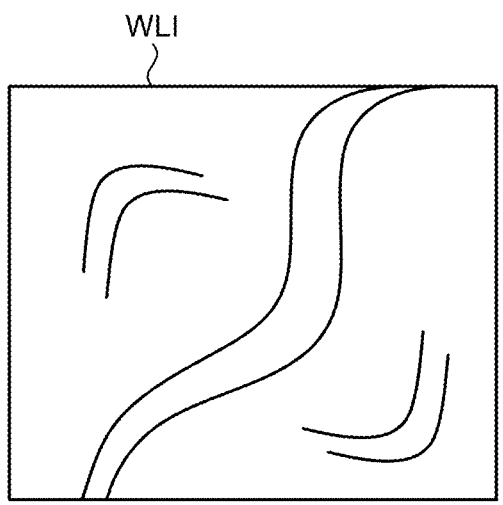
FIG. 11 is a diagram describing the operation of the control device.
Figure 12:
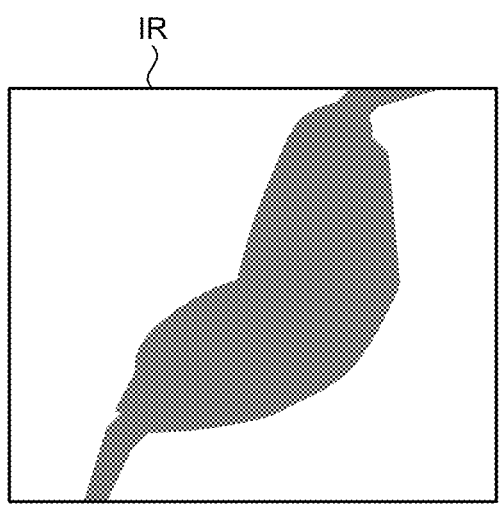
FIG. 12 is a diagram describing the operation of the control device.
Figure 13:
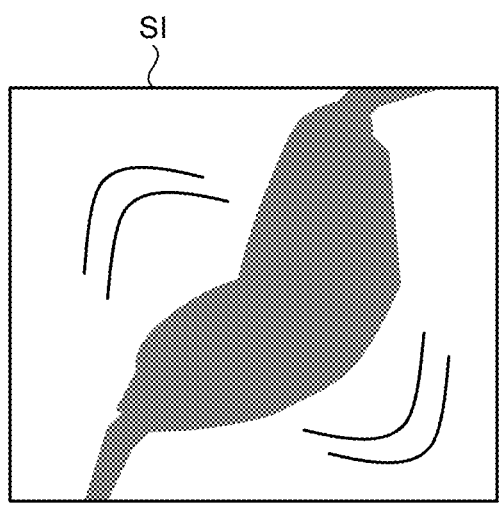
FIG. 13 is a diagram describing the operation of the control device.

FIG. 10 is a flowchart illustrating the operation of the control device 9. FIG. 11 to FIG. 13 are diagrams illustrating the operation of the control device 9. Specifically, FIG. 11 is a diagram describing an object image WLI of one frame after the first image processing is executed. FIG. 12 is a diagram illustrating a fluorescent image IR of one frame after the second image processing is executed. Note that, the fluorescent image IR illustrated in FIG. 12 is represented by a gray scale, and the intensity of the captured fluorescent component increases as being close to black (a luminance value is high). FIG. 13 is a diagram illustrating a superimposed image D1 of one frame that is generated by the superimposed image generating unit 933.

First, the light source controller 941 executes time-division drive with respect to the first light source 31 and the second light source 32 (Step S1). Specifically, in Step S1, in the first period and the second period that are alternately repeated, the light source controller 941 emits light from the first light source 31 in the first period, and emits light from the second light source 32 in the second period, based on the synchronization signal.

After Step S1, in the first period and the second period, the imaging controller 942 allows the image sensor 522 to capture each of the object picture and the fluorescent picture, in synchronization with the light emitting timing of the first light source 31 and the second light source 32, based on the synchronization signal (Steps S2 to S4). That is, in the case of the first period (Step S2: Yes), in other words, in a case where the inside of the biological body is irradiated with the normal light (the white light), the image sensor 522 generates the object image by capturing the object picture (the normal light) (Step S3). On the other hand, in the case of the second period (Step S2: No), in other words, in a case where the inside of the biological body is irradiated with the near-infrared excitation light, the image sensor 522 generates the fluorescent image by capturing the fluorescent picture (the fluorescence) (Step S4).

After Steps S3 and S4, the memory controller 931 controls the writing and the reading of the RAW captured image with respect to the memory 92, based on the synchronization signal (Step S5).

After Step S5, the image processor 932 executes the following processing (Step S6).

That is, the image processor 932 sequentially executes the first image processing with respect to the each of the RAW captured images D0 (the object images) sequentially read out from the memory 92 by the memory controller 931. In addition, the image processor 932 sequentially executes the second image processing with respect to each of the RAW captured images D0 (the fluorescent images) sequentially read out from the memory 92 by the memory controller 931.

After Step S6, the superimposed image generating unit 933 sequentially generates the superimposed image (for example, a superimposed image SI illustrated in FIG. 13) by superimposing images corresponding to each of the object images (for example, an object image WLI illustrated in FIG. 11) to be sequentially output from the image processor 932 and each of the fluorescent images (for example, a fluorescent image IR illustrated in FIG. 12) to be sequentially output from the image processor 932 in pixels corresponding to the entire region (Step S7).

After Step S7, the display controller 934 sequentially generates a video signal for displaying each of the superimposed images (for example, the superimposed image SI illustrated in FIG. 13) sequentially generated by the superimposed image generating unit 933, and sequentially outputs the video signal to the display device 7 (Step S8). Accordingly, the superimposed image (for example, the superimposed image SI illustrated in FIG. 8) is sequentially displayed on the display device 7.

According to this embodiment described above, the following effects are obtained.

In the control device 9 according to this embodiment, the first signal path for executing the first image processing with respect to the input RAW captured image D0 (the object image) and the second signal path for executing the second image processing with respect to the input RAW captured image D0 (the fluorescent image) are provided in the image processor 932. Then, the second signal path is a path diverged from the first signal path on the path former part from the demosaic processor 9322, in which the demosaic processing is not executed.

Therefore, when the luminance color difference signal based on the fluorescent image is generated, it is possible to use the r value, the g value, and the b value that are actually detected by the image sensor 522, without using the pixel data generated by the interpolation, and thus, the sharpness of the fluorescent image IR does not decrease. That is, it is possible to generate an image suitable for observation (the fluorescent image IR).

In particular, each of the filter groups 522r, 522g, and 522b of R, G, and B has approximately the same spectroscopic properties, in the wavelength band of the fluorescence (the second wavelength band). In addition, the RAW captured image D0 (the fluorescent image) obtains a white balance of the r value, the g value, and the b value by the WB processing, in the wavelength band of the fluorescence. For this reason, it is possible to input three fluorescent images D0' after the WB processings that are identical to each other into the signal generating unit 9326 and to generate the luminance color difference signals Y, Cb, and Cr by the signal generating unit 9326, without performing the demosaic processing with respect to the RAW captured image D0 (the fluorescent image).

In addition, the second signal path is converged into the first signal path on the path latter part from the demosaic processor 9322. Then, the signal generating unit 9326 is provided in the path to which the first signal path and the second signal path are converged. In addition, the selector 9323 is provided between the demosaic processor 9322 and the signal generating unit 9326.

For this reason, the number of selectors 9323 is minimized, and thus, it is possible to process two types of RAW captured images D0 (the object image and the fluorescent image) by the image processor 932, without increasing a circuit size of the image processor 932.

Other Embodiments

The mode for carrying out the present disclosure has been described, but the present disclosure is not limited to the embodiment described above.

Figure 14:
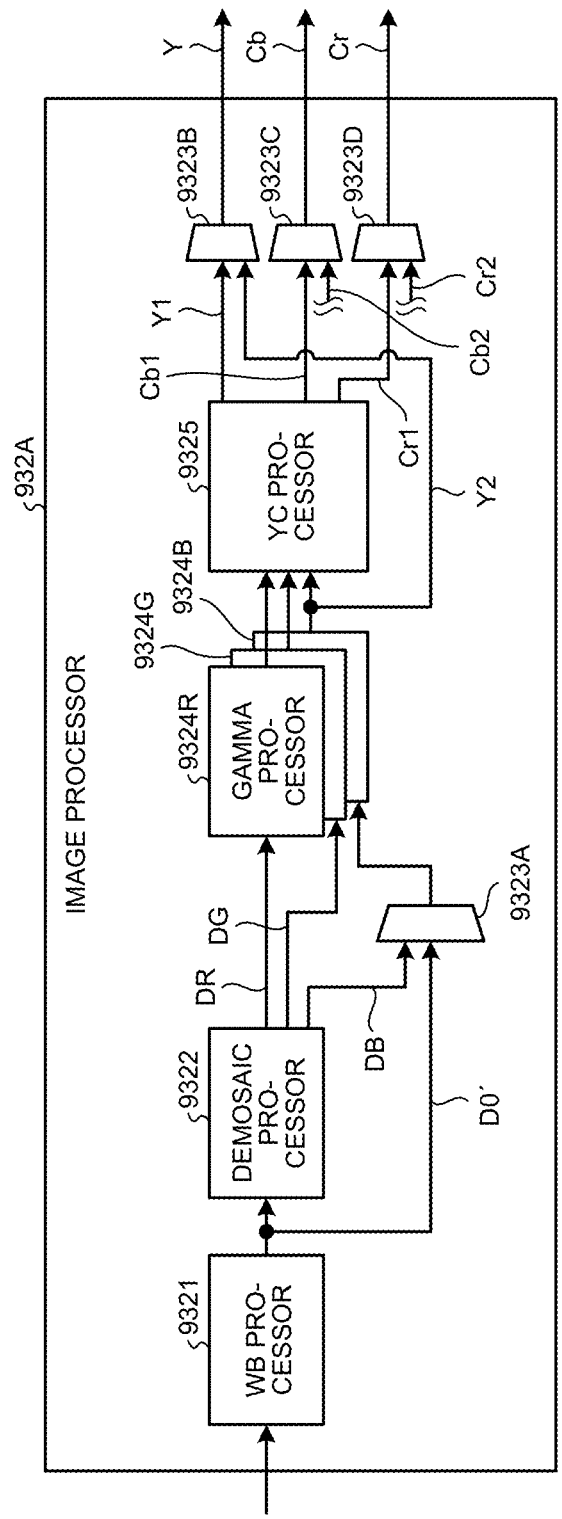
FIG. 14 is a diagram illustrating a modification example of the embodiment.

FIG. 14 is a diagram illustrating a modification example of this embodiment. Specifically, FIG. 14 is a block diagram illustrating the configuration an image processor 932A according to this modification example.

In the embodiment described above, the image processor 932A illustrated in FIG. 14 may be adopted instead of the image processor 932.

In the image processor 932A, first to fourth selectors 9323A to 9323D are adopted instead of the selector 9323.

The first selector 9323A is provided between the demosaic processor 9322 and the gamma processor 9324B. Then, the first selector 9323A outputs one image of the B captured image DB that is input from the demosaic processor 9322, and the fluorescent image D0' after the WB processing that is input from the WB processor 9321, to the gamma processor 9324B, under the control of the control unit 94.

The second selector 9323B is provided on the path latter part from the YC processor 9325. Then, the second selector 9323B outputs one of a luminance signal Y1 (FIG. 14) that is generated by allowing the YC processor 9325 to perform calculation in a specific arithmetic expression by using three R, G, and B captured images DR, DG, and DB subjected to the gamma processing, and a fluorescent image Y2 (FIG. 14) after the gamma processor 9324B executes the gamma processing with respect to the fluorescent image D0', as the luminance signal Y, under the control of the control unit 94. Note that, in a case where the fluorescent image Y2 is output as the luminance signal Y, any of the r value, the g value, and the b value that are provided for each pixel is directly output as the luminance value.

The third selector 9323C is provided on the path latter part from the YC processor 9325. Then, the third selector 9323C outputs one of a color difference signal Cb1 (FIG. 14) that is generated by allowing the YC processor 9325 to perform calculation in a specific arithmetic expression by using three R, G, and B captured images DR, DG, and DB subjected to the gamma processing, and a signal Cb2 indicating 0, as the color difference signal Cb, under the control of the control unit 94. Note that, in a case where the second selector 9323B outputs the luminance signal Y1 as the luminance signal Y, the third selector 9323C outputs the color difference signal Cb1 as the color difference signal Cb, and in a case where the second selector 9323B outputs the fluorescent image Y2 as the luminance signal Y, the third selector 9323C outputs the color difference signal Cb2 as the color difference signal Cb, under the control of the control unit 94.

The fourth selector 9323D is provided on the path latter part from the YC processor 9325. Then, fourth selector 9323D outputs one of a color difference signal Cr1 (FIG. 14) that is generated by allowing the YC processor 9325 to perform calculation in a specific arithmetic expression by using three R, G, and B captured images DR, DG, and DB subjected to the gamma processing, and a signal Cr2 indicating 0, as the color difference signal Cr, under the control of the control unit 94. Note that, in a case where the second selector 9323B outputs the luminance signal Y1 as the luminance signal Y, the fourth selector 9323D outputs the color difference signal Cr1 as the color difference signal Cr, and in a case where the second selector 9323B outputs the fluorescent image Y2 as the luminance signal Y, the fourth selector 9323D outputs the color difference signal Cr2 as the color difference signal Cr, under the control of the control unit 94.

As described above, in this modification example, the first signal path for executing the first image processing with respect to the input RAW captured image D0 (the object image) and the second signal path for executing the second image processing with respect to the input RAW captured image D0 (the fluorescent image) are provided in the image processor 932A. The first signal path is a path following the WB processor 9321 to the demosaic processor 9322 to the first selector 9323A to three gamma processors 9324R, 9324G, and 9324B to the YC processor 9325 to the second selector 9323B, the third selector 9323C, and the fourth selector 9323D. On the other hand, the second signal path is a path following the WB processor 9321 to the first selector 9323A to the gamma processor 9324B to the second selector 9323B. That is, the second signal path is a path diverged from the first signal path on the path former part from the demosaic processor 9322, in which the demosaic processing is not executed.

Even in a case where the image processor 932A according to this modification example described above is adopted, the same effects as those of the embodiment described above are obtained.

Note that, in the modification example described above, the first selector 9323A inputs the B captured image DB and the fluorescent image D0', and outputs one of the images to the gamma processor 9324B, but the present disclosure is not limited thereto. For example, the first selector 9323A may input the R captured image DR and the fluorescent image D0', and may output one of the images to the gamma processor 9324R. At this time, the second selector 9323B inputs the luminance signal Y1, and the fluorescent image after the gamma processor 9324R executes the gamma processing with respect to the fluorescent image D0', and outputs one of the images as the luminance signal Y. In addition, for example, the first selector 9323A may input the G captured image DG and the fluorescent image D0', and may output one of the images to the gamma processor 9324G. At this time, the second selector 9323B inputs the luminance signal Y1, and the fluorescent image after the gamma processor 9324G executes the gamma processing with respect to the fluorescent image D0', and outputs one of the images as the luminance signal Y.

In the embodiment described above, the first light source 31 emits the white light, and the second light source 32 emits the near-infrared excitation light, but the present disclosure is not limited thereto. Other configurations may be adopted as the first light source 31 and the second light source 32, insofar as the first light source 31 emits the light of the first wavelength band, and the second light source 32 emits the light of the third wavelength band different from the first wavelength band. At this time, the first wavelength band and the third wavelength band may be a band in which the wavelength bands overlap each other in a part, or a band in which the wavelength bands do not overlap each other. In addition, the first light source 31 may emit light of a narrowband.

In the embodiment described above, the first period and the second period are set to be alternately repeated, but the present disclosure is not limited thereto, and at least any of the first period and the second period may be continuous, and a frequency ratio of the first period to the second period may be a ratio other than 1:1.

In the embodiment described above, the spectroscopic properties of each of the filter groups configuring the color filter 522a are not limited to the spectroscopic properties illustrated in FIG. 4, and a color filter having other spectroscopic properties may be adopted.

In the embodiment described above, the medical image processing apparatus according to the present disclosure is mounted in the medical observation system 1 in which the insertion portion 2 is configured as a rigid endoscope, but the present disclosure is not limited thereto. For example, the medical image processing apparatus according to the present disclosure may be mounted in a medical observation system in which the insertion portion 2 is configured as a flexible endoscope. In addition, the medical image processing apparatus according to the present disclosure may be mounted in a medical observation system such as a surgical microscope that performs observation by enlarging a predetermined visual field region in the object (in the biological body) or on the surface of the object (the surface of the biological body) (for example, refer to JP 2016-42981 A).

In the embodiment described above, a part of the configuration of the camera head 5 or a part of the configuration of the control device 9, for example, may be provided in the connector CN1 or the connector CN2.

In the embodiment described above, the superimposed image (for example, the superimposed image SI illustrated in FIG. 13) is generated by superimposing the object image after being subjected to the first image processing (for example, the object image WLI illustrated in FIG. 11) and the fluorescent image after being subjected to the second image processing (for example, the fluorescent image IR illustrated in FIG. 12) in the corresponding pixels, and the superimposed image is displayed on the display device 7, but the present disclosure is not limited thereto. For example, picture-in-picture processing or the like may be executed, and the object image and the fluorescent image may be simultaneously displayed on the display device 7.

According to the medical image processing apparatus and the medical observation system of the present disclosure, it is possible to generate an image suitable for observation.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical image processing apparatus comprising:
   image signal acquiring circuitry configured to acquire:
     a first image signal generated by capturing light of a first wavelength band with an image sensor; and
     a second image signal generated by capturing light of a second wavelength band different from the first wavelength band with the image sensor, the first image signal and the second image signal being not subjected to demosaic processing, and the image sensor including a color filter in which a plurality of filter groups having spectroscopic properties different from each other are arranged in a specific form on a light receiving surface of the image sensor; and
   image processing circuitry including
     a first signal path including a demosaic processor configured to execute the demosaic processing to the first image signal acquired by the image signal acquiring circuitry and input into the first signal path;
     a second signal path diverged from the first signal path on a path separate from the demosaic processor, in which the demosaic processing is not executed to the second image signal acquired by the image signal acquiring circuitry and input into the second signal path; and a converged signal path after the demosaic processor in which the first and second signal paths are converged and provided to signal generating circuitry configured to generate luminance signals.

2. The medical image processing apparatus according to claim 1, wherein the image signal acquiring circuitry is configured to acquire:

the first image signal generated by capturing the light of the first wavelength band with the image sensor including the color filter in which a first filter group that most transmits light of a first visible wavelength band in the first wavelength band that is a visible wavelength band, and transmits the light of the second wavelength band that is a wavelength band other than a visible range, and a second filter group that most transmits light of a second visible wavelength band different from the first visible wavelength band in the first wavelength band, and transmits the light of the second wavelength band are arranged in the specific form; and the second image signal generated by capturing the light of the second wavelength band with the image sensor.

3. The medical image processing apparatus according to claim 2, wherein the second signal path includes output circuitry configured to output a plurality of the second image signals that are identical to each other, wherein the signal generating circuitry is configured to generate a luminance color difference signal from the plurality of second image signals that are output from the output circuitry.

4. The medical image processing apparatus according to claim 3, further comprising a selector, wherein in the first signal path, a plurality of demosaic image signals corresponding to each filter group of the plurality of filter groups are generated by the demosaic processor, the second signal path is converged into the first signal path on a path latter part from the demosaic processor, the selector is disposed in the converged signal path, the plurality of demosaic image signals and the plurality of second image signals are input into the selector, the selector is configured to output any one image signal of the plurality of demosaic image signals and the plurality of second image signals, and the signal generating circuitry is configured to generate a luminance color difference signal based on the image signal output from the selector.

5. The medical image processing apparatus according to claim 1, further comprising a white balance adjustment processor configured to execute white balance adjustment processing, the white balance adjustment processor being provided in a path before being diverged into the first signal path and the second signal path.

6. The medical image processing apparatus according to claim 1, wherein the second signal path includes output circuitry configured to output a plurality of the second image signals that are identical to each other, and signal generating circuitry configured to generate a luminance color difference signal from the plurality of second image signals that are output from the output circuitry.

7. The medical image processing apparatus according to claim 6, further comprising a selector, wherein in the first signal path, a plurality of demosaic image signals corresponding to each filter group of the plurality of filter groups are generated by the demosaic processor, the second signal path is converged into the first signal path on a path latter part from the demosaic processor, the selector is disposed in the converged signal, the plurality of demosaic image signals and the plurality of second image signals are input into the selector, the selector is configured to output any one image signal of the plurality of demosaic image signals and the plurality of second image signals, and the signal generating circuitry is configured to generate a luminance color difference signal based on the image signal output from the selector.

8. The medical image processing apparatus according to claim 7, further comprising a white balance adjustment processor configured to execute white balance adjustment processing, the white balance adjustment processor being provided in a path before being diverged into the first signal path and the second signal path.

9. The medical image processing apparatus according to claim 1, further comprising:

an imaging device including the image sensor configured to generate the first image signal by capturing light of the first wavelength band, and generate the second image signal by capturing light of the second wavelength band, and the color filter provided on the light receiving surface of the image sensor, in which the plurality of filter groups having spectroscopic properties different from each other are arranged in the specific form.

10. The medical image processing apparatus according to claim 9, wherein the color filter includes;

a first filter group that most transmits light of a first visible wavelength band in the first wavelength band that is a visible wavelength band, and transmits the light of the second wavelength band that is a wavelength band other than a visible range; and a second filter group that most transmits light of a second visible wavelength band different from the first visible wavelength band in the first wavelength band, and transmits the light of the second wavelength band are arranged in the specific form, and the image signal acquiring circuitry is configured to acquire the first image signal that is generated by receiving the light of the first visible wavelength band and the light of the second visible wavelength band from a subject with the image sensor, and is not subjected to the demosaic processing, and the second image signal that is generated by receiving the light of the wavelength band other than the visible range from the subject with the image sensor, and is not subjected to the demosaic processing.

11. The medical image processing apparatus according to claim 10, wherein the second signal path includes output circuitry configured to output a plurality of the second image signals that are identical to each other, wherein the signal generating circuitry is configured to generate a luminance color difference signal from the plurality of second image signals that are output from the output circuitry.

12. The medical image processing apparatus according to claim 11, further comprising a selector, wherein in the first signal path, a plurality of demosaic image signals corresponding to each filter group of the plurality of filter groups are generated by the demosaic processor,
the second signal path is converged into the first signal path on a path latter part from the demosaic processor,
the selector is disposed in the converged signal path,
the plurality of demosaic image signals and the plurality of second image signals are input into the selector,
the selector is configured to output any one image signal of the plurality of demosaic image signals and the plurality of second image signals, and
the signal generating circuitry is configured to generate a luminance color difference signal based on the image signal output from the selector.

13. The medical image processing apparatus according to claim 12, further comprising a white balance adjustment processor configured to execute white balance adjustment processing, the white balance adjustment processor being provided in a path before being diverged into the first signal path and the second signal path.

14. The medical image processing apparatus according to claim 9, wherein the second signal path includes
output circuitry configured to output a plurality of the second image signals that are identical to each other, and
signal generating circuitry configured to generate a luminance color difference signal from the plurality of second image signals that are output from the output circuitry.

15. The medical image processing apparatus according to claim 14, further comprising a selector, wherein
in the first signal path, a plurality of demosaic image signals corresponding to each filter group of the plurality of filter groups are generated by the demosaic processor,
the selector is disposed in the converged signal path,
the plurality of demosaic image signals and the plurality of second image signals are input into the selector,
the selector is configured to output any one image signal of the plurality of demosaic image signals and the plurality of second image signals, and
the signal generating circuitry is configured to generate a luminance color difference signal based on the image signal output from the selector.

16. The medical image processing apparatus according to claim 15, further comprising a white balance adjustment processor configured to execute white balance adjustment processing, the white balance adjustment processor being provided in a path before being diverged into the first signal path and the second signal path.

17. The medical image processing apparatus according to claim 9, further comprising a white balance adjustment processor configured to execute white balance adjustment processing, the white balance adjustment processor being provided in a path before being diverged into the first signal path and the second signal path.

18. The medical image processing apparatus according to claim 1, further comprising:
superimposing circuitry configured to superimpose luminance signals from the first signal path and luminance signals from the second signal path.

* * * * *